United States Patent

Kuchar et al.

Patent Number: 5,177,204
Date of Patent: Jan. 5, 1993

[54] DERIVATIVES OF 4-(2,4-DIFLUORBIPHENYLYL)-2-METHYL-4-OXOBUTANOIC ACID

[75] Inventors: Miroslav Kuchař; Marie Poppová; Jaroslava Grimová; Eva Maturová, all of Praha, Czechoslovakia

[73] Assignee: Vyzkumng, ÛSTAV pro farmacii a biochemii, Státni podnik, Praha, Czechoslovakia

[21] Appl. No.: 716,814

[22] Filed: Jun. 17, 1991

[30] Foreign Application Priority Data

Jun. 18, 1990 [CS] Czechoslovakia ............ 3027-90

[51] Int. Cl.$^5$ .............. C07C 59/88; C07C 69/738; C07C 235/34; C07D 295/192
[52] U.S. Cl. .............. 544/126; 560/51; 562/459; 564/169
[58] Field of Search ............ 562/459; 544/126; 564/169; 560/51

[56] References Cited

U.S. PATENT DOCUMENTS 4,683,331  7/1987  Kuchar ............... 562/459

Primary Examiner—Robert Gerstl
Attorney, Agent, or Firm—McGlew and Tuttle

[57] ABSTRACT

This relates to substances represented by formula (I), wherein X stands for represented by either OR in which R is an alkyl of 1 to 4 carbon atoms, or NHR in which is an alkyl of 1 to 4 carbon atoms, or a $(CH_2)_nNR_2$ group wherein n is 2 or 3 while R is an methyl or an ethyl group; eventually X may represent morpholinyl. Also considered are salts of 4-(2,4-difluorbiphenylyl)-2-methyl-4-oxobutanoic acid with appropriate inorganic or organic bases represented by formula (II) wherein B+ is either an alkaline metal cation, alkaline earth metal cation, cyclohexylamine cation, or lysine cation. Said substances are characterized by antiinflamatory properties comparable to (and greater than) the initial acid while simultaneously said modifications of their physico-chemical properties broaden the posibilities of their therapeutic application.

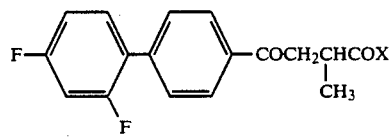

I

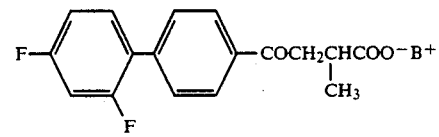

II

9 Claims, No Drawings

DERIVATIVES OF 4-(2,4-DIFLUORBIPHENYLYL)-2-METHYL-4-OXOBUTANOIC ACID

This invention relates to 4-(2,4-difluorbiphenylyl)-2-methyl-4-oxobutan acid having the following general formula

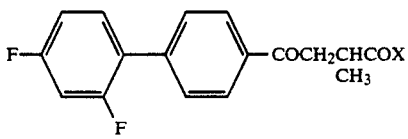

wherin X stands for OR in which R is an alkyl of 1 to 4 carbon atoms, or NHR in which R is an alkyl of 1 to 4 carbon atoms, or a $(CH_2)_n NR'_2$ group wherein n is 2 or 3 while R' is a methyl or an ethyl group; eventually X may represent morpholinyl. This invention further relates to salts of 4-(2,4-difluorbiphenylyl)-2-methyl-4-oxobutan acid with appropriate inorganic or organic bases represented by general formula (II)

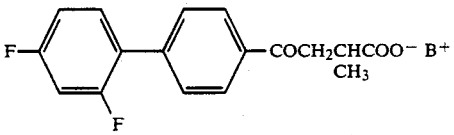

wherein $B^+$ etither an alkaline metal cation, alkaline earth cation, cyclohexylamine cation, or lysine cation.

Recently a significant prolonged anti-inflammatory efect of 4-(2-4-difluorbiphenylyl)-2-methyl-4-oxobutan acid (Cs. A0 243 570, 1988) has been recognized. An analogous anti-inflammatory effect was found in several functional derivatives and salts of said acid. Some of the substances of general formula (I) and (II) are cahracterized by physico-chemical properties, incl. increased solubility in water, which broaden their therapeutic application without any noticable decrease in their anti-inflammatory effect. Changes in lipophility eventually differing biotransformation of esters and amides in comparison with the free acid may influence the pharmacokinetic behaviour of these derivatives. Results of the pharmacological evaluation of substances (I) and (II) are summarized in table (I). Simultaneously these substances an characterized by low toxicity, incl. a low ulcerogenic effect. They may be used for the preparation of therapeutic compositions which may contain the effective substance in combination with pharmacologically acceptable ingredients, liquid or solid, which are usually used in the manufacture of application forms.

EXAMPLE 1

Ethoxycarbonylmethylamid (4-(2,4-Difluorbiphenylyl)-2-methyl-4-Oxobutan Acid

In a mixture of 35 ml dimethylformamide and 150 ml dichlormethane is dissolved 5.0 g of 4-(2,4-difluorbiphenylyl)-2-methyl-4-oxobutan acid. 2.1 g N-ethyl-piperidine is added to the solution and 2.05 g ethylchloroformiate is added after cooling to $-15°$ C. After stirring for 30 min. at $-15°$ C. the mixture is cooled to $-30°$ C. and 1.7 g glycineethylester in 35 ml dichloromethane is added. The mixture is left at room temperature to warm up to 20° C. and at this temperature it is stirred for 2 hours. Thereafter, in a separation funnel, the mixture is consecutively washed 3 times in 100 ml, 5% $NaHCO_3$, once in 100 ml $H_2O$, 3 times in 100 ml 1N HCl, and once again in 100 ml $H_2O$.

Water is adsorbed by $Na_2SO_4$ from the organic part which is then dried by evaporation and the crystalline residue is purified by crystallization in acetone. 4.3 g /67.2% theor./ of the ethoxycarbonylmethylamide with a melting point of 95°–96° C.; for $C_{21}H_{21}NF_2O_4$ /389.4/ calculated: 64.77% C, 5.44% H, 3.58% N, 9.76% F, found: 64.84% C, 5.35% H, 3.34% N, 9.66% F, $^1H$-NMR /$C^2HCl_3$/: /2-$CH_3$/=1.30 d, J=7.0 Hz; /NH/=6.36 bt; /aromat. ortho-CH/=8.05 d, J=8.5 Hz.

Similarly were prepared:

Ethylamide of 4-/2,4-difluorobiphenylyl/-2-methyl-4-oxobutan acid with a 72,8% recovery with melting point 128° C. /acetone crystallized/; for $C_{19}H_{19}NF_2O_2$ /331.4/ calculated was: 64.77% C, 5.44% H, 3.58% N, 9.76% F, found was: 64.84% C, 5.35% H, 3.34% N, 9.66% F, $^1H$-NMR /$C^2HCl_3$/: /2-$CH_3$/=1.30 d, J=7.0 Hz; /NH/=6.36 bt; /aromat. ortho-CH/=8.05 d, J=8,5 Hz.

Morpholide of 4-/2,4-difluorobiphenylyl/-2-methyl-4-oxobutan acid with a 65.8% recovery with melting point of 95°–97° C. /crystallized in acetone/ /n-hexane, 4:1/; for $C_{21}H_{21}NF_2O_3$ /373.4/ calculated: 67.55% C, 5.69% H, 3.75% N, 10.18% F; found was: 67.36% C, 5.81% H, 3.66% N, 10.29% F; $^1H$-NMR /$C^2HCl_3$/: /2-$CH_3$/=1.22 d, J=7.0 Hz; /$CH_2$ morpholine=3,68 bs; /aromat. ortho-CH/=8.07 d, J==8.5 Hz.

EXAMPLE 2

Ethylester of 4-/2,4-Difluorobiphenylyl-4-oxobutan acid 1.2 ml thionylchloride is added to 20 ml ethanol cooled to $-15°$ C. and thereafter 4.0 g 4-/2,4-difluorobiphenylyl/-2-methyl-4-oxobutan acid is added in four portions while the temperature is kept at $-10°$ C. by cooling. At this temperature it is stirred for another 30 minutes, thereafter instead of cooling then mixture is heated to 40°–45° C. for 2 hours. Ethanol is vacuum evaporated and the residue is dried by double vacuum distillation with 20 ml benzene. After crystallization in acetone the crude produce gives 3.0 g /68.5% theor./ of ethylester with melting point of 67°–68° C.; for $C_{19}H_{18}F_2O_3$ /332.4/ calculated was: 68.66% C, 5.46% H, 11.43% F, found was: 68.41% C, 5.41% H, 11,37% F, $^1H$-NMR /$C^2HCl_3$/: /2-$CH_3$/=1,30 d, J=7.0 Hz; /$CH_2$ ester/=4.16 q, J=7.0 Hz; /arom. ortho-CH/=8.06, J=8.5 Hz.

Similarly was prepared:

Isobutylester of 4-/2,4-difluorobiphenylyl/-2-methyl-4-oxobutan acid with a 90.5% recovery with melting point of 50°–52° C.; for $C_{21}H_{22}F_2O_3$ /360.4/ calculated was: 69.98% C, 6.15% H, 10.54% F, found was: 69.78% C, 6.16% H, 10.28% F, $^1H$-NMR /$C^2HCl_3$: /$CH_3$ isobutyl/=0.92 d, J=7.0 Hz/; /2-$CH_3$/=1.30 d, J=7.0 Hz; /aromat.ortho-CH/=8.08 d, J=8.5 Hz.

EXAMPLE 3 n-Butylamide of 4-/2,4-Difluorobiphenylyl/-2-methyl-4-oxobutan Acid 0.2 ml dimethylformamide is added to a suspension of 6.0 g 4-/2,4-difluorobiphenylyl/-2-methyl-4-oxobutan acid in 40 ml benzene and thereafter within 10 minutes 20 ml solution of thionylchloride in 20 ml benzene is added, thereafter, the mixture is heated to boiling /the suspension become a solution/ and is kept at this temperature while stirring for 45 minutes. The reaction mixture is vacuum condensed and the residue is redissolved in 50 ml benzene and condensed until dry. The thus obtained chloride of 4-/2,4-difluorobiphenylyl/-2-methyl-4-oxobutan acid is mixed with 50 ml benzene and the solution is filtered with activated carbon. The clear filtrate is slowly added under constant stirring to a solution of 2.90 g of n-butylamine in 20 ml benzene cooled to 5° C. The mixture is then kept for 1 hour at 5° C. and 2 hours at 20° C. The opaque solution is washed consecutively in 100 ml 1N HCl, 100 ml $H_2O$, twice in 100 ml 5% $NaHCO_3$ and again in 100 ml $H_2O$. After drying with magnesiumsuphate the benzene is distilled off in vacuum and the crude product is crystallized in acetone. n-butylamide of 4-/2,4-difluorobiphenylyl/-2-methyl-4oxobutan acid with melting point 114°-115° C. and recovery of 72.5% is obtained. For $C_{21}H_{23}F_2NO_2$ /359.4/ calculated was: 70.18% C, 6.45% H, 3.90% N, 10.57% F; found was: 70.40% C, 6.60% H, 3.89% N, 10.44% F, $^1H$ NMR /$C^2HCl_3$/: /2-$CH_3$/=1.25 d, J=7.0 Hz; /NH/=5.86 bt; /aromat. ortho-CH/=8.06 d, J=8.5 Hz.

EXAMPLE 4

Cyclohexylammonium Salt of 4-/2,4-Difluorobiphenylyl/-2-methyl-4-oxobutan Acid 4.0 g of 4-/2,4-difluorobiphenylyl/-2-methyl-4-oxobutan acid is dissolved in 40 ml acetone and to the clear solution is added under constant stirring and cooling at 20° C. a solution of 1.32 g cyclohexylamine in 20 ml ether. Immediately a sediment begins to precipitate and end after 2 hours of cooling at 0° C. The precipitate is removed and is thoroughly washed in cooled acetone. Obtained is 4.6 g /86.1% theoret./ of the sought product with melting point of 139°-140° C.; for $C_{23}H_{27}F_2O_3$ /403.5/ calculated was: 68.47% C, 6.75% H, 3.47% N, 9.42% F; found was: 68.18% C, 6.74% H, 3.42% N, 9.25% F.

EXAMPLE 5

Potassium Salt of 4-/2,4-Difluorobiphenylyl/-2-methyl-4-oxobutan Acid

To a solution of 3.05 g 4-/2,4-difluorobiphenylyl/-2-methyl-4-oxobutan acid in 30 ml acetone a solution of 0.5 g KOH in 10 ml methanol is added. The solution is evaporated to an oily residue which gives an amorphous precipitate by mixing in 40 ml ether. The precipitate is dissolved in 60 ml ethanol, the opaque solution is filtered with activated carbon and the clear filtrate is again evaporated. The oily residue is mixed with 40 ml ether and the precipitate is recovered by filtration. 2.35 g /65.3% theoret./ of potassium salt as a monohydrate with melting point of 173°-174° C. is obtained. For $C_{17}H_{13}F_2O_3K.H_2O$ /360.4/ calculated was: 56.65% C, 4.19% H, 10.54% F; found was: 56.71% C, 4.04% H, 10.39% F.

EXAMPLE 6

Calcium salt of 4-2,4-Difluorobiphenylyl/-2-methyl-4-oxo-butan Acid 3.05 g of 4-/2,4-difluorobiphenylyl/-2-methyl-4-oxobutan acid is dissolved in 55 ml 5N NaOH at 40° C. and the clear solution is heated to 70° C. and gradually a solution of 1.1 g $CaCl_2$ is added. Upon cooling to 5° C. a precipitate is formed which after 2 hours of standing at this temperature is removed and washed on a filter with distilled water until a negative reaction for chloride ions is obtained. The precipitate is then resuspended in 50 ml distilled water and then pH is adjusted to 8 with 1N HCl under constant stirring, it is mixed for another 30 minutes and the precipitate is removed; upon drying to a constant weight 2.7 g /83.6% theoret./ of calcium salt of 4-2,4-difluorobiphenylyl/-2-methyl-4-oxo-butan Acid 4.0 g of 4-2,4-difluorobiphenylyl/-2-methyl-4-oxobutan acid is dissolved in 70 ml acetone at 40° C. under constant stirring. After cooling to 20° C. a solution of 2.15 g L-lysine in 10 ml $H_2O$ is added to the clear solution. The mixture is cooled to 5° C. and after stirring for 2 hours at this temperature the precipitate found is removed and washed in 10 ml cooled acetone. Upon drying to a constant weight 3.5 g /59.1% theoret./ of the product with melting point 173°-175° C. is obtained. For $C_{23}H_{28}N_2F_2O_5$ /450,5/ calculated was: 61,32% C, 6.26% H, 6.22% N, 8.43% F; found was: 61.13% C, 6.43% H, 6.01% N, 8.26% F.

TABLE I

Pharmacological evaluation of acute toxicity[a] anti-inflammatory effect[b] in the suppression of carragenine oedema (CE) and in the inhibition of adjuvant oedema (FA) and analgesic action.

| Substance No. | Formula I (II) X (B+) | % mortality | CE[c] inhibition % | FA[d] inhibition % | Pain[e] inhibition % |
|---|---|---|---|---|---|
| VÚFB 18391 | $C_2H_5O$ | 0 | 49 | 55 | 38 |
| VÚFB 18392 | $C_2H_5OCOCH_2NH$ | 0 | 40 | 51 | 41 |
| VÚFB 18398 | $n-C_4H_9NH$ | 0 | 33 | 44 | 33 |
| VÚFB 17629 | $(o-C_6H_{11}NH_3^+)$ | 0 | 47 | 53 | 58 |
| VÚFB 18404 | $(Na^+)$ | 30 | 44 | 51 | 35 |
| VÚFB 18405 | $(K^+)$ | 20 | 39 | 50 | 47 |
| Flobufen[f] | OH | 50 | 46 | 65 | 79 |

[a]Acute oral toxicity of each substance was evaluated after a single dose of 500 mg/kg in male mice. The mortality in % is for day 7 after application;
[b]Anti-inflammatory and analgesic activity was evaluated in comparison with flobufen in equimolar doses, while flobufen was administered in a dose of 20 mg/kg in the evaluation of anti-inflammatory activity and in a dose of 100 mg/kg in the evaluation of analgesic activity; the substances were administered orally as a suspension in a 0.5% solution of methylcellulose and the oedema was measured 1 hour upon application;
[c]Suppression of the carraganine oedema was assessed according to Winter J.: Proc. Soc. exptl. Biol. Med., 111, 544 (1962);
[d]Anti-inflammatory effect in the Freund-adjuvant test was assessed according to Horáková Z., Grimova J.: Cs. Fysiol. 17, 137 (1968);
[e]Analgesic activity was evaluated in the test of intraperitoneal irritation with 0.7% acid in male mice according to Witkin L. et al.: J. Pharmacol. 133, 400 (1961);
[f]4-(2,4-difluorobiphenylyl)-2-methyl-4-oxobutanic acid.

TABLE II

Pharmacological evaluation of acute toxicity, anti-inflammatory and analgesic activity of substance VÚFB 17640 (L-lysine salt) upon oral and parenteral application

| Mode of application | Substance | Acute toxicity[a] Dose | % mortality | CE suppression[b] Dose | % | FA suppression[b] Dose | % | Pain suppression[b] Dose | % |
|---|---|---|---|---|---|---|---|---|---|
| Oral | 17640 | 500 | 0 | 30 | 46 | 30 | 58 | 150 | 77 |
|  | Flobufen[c] | 500 | 50 | 20 | 46 | 20 | 65 | 100 | 79 |
| Parenteral | 17640 | 100 | 0 | 1 | 21 |  |  | 80 | 48 |
|  |  |  |  | 10 | 40 |  |  |  |  |

[a]Acute toxicity was evaluated after a single dose of substance 17640 in male mice, namely orally as an aqueous solution, and intravenously in physiological saline solution. Mortality was followed up in groups of 10 animals for 7 days upon oral application and for 3 days upon intravenous application;
[b]for oral and intramuscular application an aqueous solution of substance 17640 was used in said dose;
[c]the standard, i.e. 4-(2,4-difluorobiphenylyl)-2-methyl-4-oxobutanic acid was administered as a suspension in a 0.5% methylcellulose solution.

What is claimed is:

1. Derivative compounds of 4-(2,4-difluorobiphenylyl)-2-methyl-4-oxobutanoic acid, selected from the group consisting of compounds of the formula

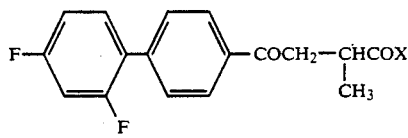

(I)

wherein X is OR in which R is an alkyl group of 1 to 4 carbon atoms, NHR in which R is an alkyl group of 1 to 4 carbon atoms, $(CH_2)_nNR'_2$ in which n is 2 or 3 and R' is a methyl or an ethyl group, or morpholinyl; and compounds of the formula

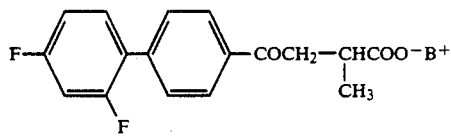

(II)

wherein B+ is a cyclohexlamine cation or a lysine cation.

2. Derivative compound of 4-(2,4-difluorobiphenylyl)-2-methyl-4-oxobutanoic acid of the formula

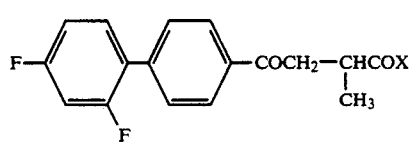

(I)

wherein X is OR in which R is an alkyl group of 1 to 4 carbon atoms, NHR in which R is an alkyl group of 1 to 4 carbon atoms, $(CH_2)_nNR'_2$ in which n is 2 or 3 and R' is a methyl or an ethyl group, or morpholinyl.

3. Compound of claim 2 wherein X is NHR, $(CH_2)_nNR'_2$, or morpholinyl.

4. Compound of claim 2 wherein X is NHR.

5. Compound of claim 2 wherein X id $(CH_2)_nNR'_2$.

6. Compound of claim 2 wherein X is the morpholide of 4-(2,4-difluorobiphenylyl)-2-methyl-4-oxobutanoic acid.

7. Derivative compound of 4-(2,4-difluorobiphenylyl)-2-methyl-4-oxobutanoic acid of the formula

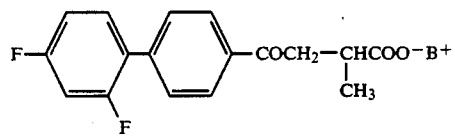

(II)

wherein B+ is a cyclohexlamine cation or a lysine cation.

8. Compound of claim 7 which is the cyclohexylammonium salt of 4-(2,4-difluorobiphenylyl)-2-methyl-4-oxobutanoic acid.

9. The L-lysine salt of 4-(2,4-difluorobiphenylyl)-2-methyl-4-oxobutanoic acid.

* * * * *

UNITED STATES PATENT AND TRADEMARK OFFICE
CERTIFICATE OF CORRECTION

PATENT NO. : 5,177,204
DATED : January 5, 1993
INVENTOR(S) : Kuchar et al

It is certified that error appears in the above-identified patent and that said Letters Patent is hereby corrected as shown below:

On the title page, Item [73] Assignee should read as follows:

[73] Assignee: Výzkumný ústav pro farmacii a biochemii, státní podnik, Praha, Czechoslovakia Signed and Sealed this Second Day of November, 1993

Attest:

BRUCE LEHMAN

Attesting Officer

Commissioner of Patents and Trademarks